United States Patent [19]

Spencer

[11] Patent Number: 5,310,877
[45] Date of Patent: May 10, 1994

[54] METHOD FOR SEPARATING SERUM ALBUMIN AND GAMMA GLOBULIN

[75] Inventor: Harold G. Spencer, Clemson, S.C.

[73] Assignee: E. I. Du Pont de Nemours and Company, Wilmington, Del.

[21] Appl. No.: 44,515

[22] Filed: Apr. 8, 1993

[51] Int. Cl.$^5$ .................. C07K 3/02; C07K 3/26; C07K 15/06

[52] U.S. Cl. .................. 530/364; 530/363; 530/387.1; 530/414; 530/390.5; 530/830; 530/832; 530/833

[58] Field of Search .......... 530/362, 363, 364, 365, 530/366, 367, 368, 369, 386, 387.1, 390.5, 414, 830, 832, 833

[56] References Cited

U.S. PATENT DOCUMENTS

| | | | |
|---|---|---|---|
| 4,347,138 | 8/1982 | Ohno et al. | 210/639 |
| 4,485,040 | 11/1984 | Roger et al. | 530/366 |
| 4,644,056 | 2/1987 | Kolthe et al. | 530/387 |
| 4,711,953 | 12/1987 | Roger et al. | 530/366 |
| 4,762,619 | 8/1988 | Gaddis et al. | 210/639 |
| 4,888,114 | 12/1989 | Gaddis et al. | 210/500.25 |
| 4,897,465 | 1/1990 | Cordle et al. | 530/387.1 |

OTHER PUBLICATIONS

Nadkarni, et al. "Preparative Separation of Fibrinogen, Gamma Globulins, Transferrin, Albumin, & Ceruloplasmin from a Single Sample of Plasma" Indian J. Biochem vol. 5 Mar. 1968, pp. 16–18.

*Primary Examiner*—Jeffrey E. Russel
*Assistant Examiner*—Nancy J. Gromet

[57] ABSTRACT

The invention is directed to a method for the separation of gamma globulin from albumin contained in an aqueous solution of both having a pH of 8–10 by ultrafiltration using an altered substrate microfilter having a water permeability of no more than 20 gallons per square foot per day per pound per square inch.

3 Claims, No Drawings

METHOD FOR SEPARATING SERUM ALBUMIN AND GAMMA GLOBULIN

FIELD OF INVENTION

The invention is directed to a method for separating proteins. In particular, the invention is directed to a method for the separation and concentration of serum albumin and gamma globulin from aqueous solutions containing both substances.

BACKGROUND OF THE INVENTION

Proteins in solution are difficult to separate from one another, particularly with their biological activity preserved. The need for simple processes is great. Isolation of specific proteins is required for industrial processes and for biological and medical research, for example. Removal of harmful proteins from foods is also a frequent problem. Consequently, there has been enormous research toward the objective. Although many methods have been developed for specific separations, the procedures are frequently difficult and time-consuming, and in some cases there is no practical process. The search for better ways continues.

Membranes have been a popular approach in recent years. Their use does not involve extreme conditions, such as the high electrolyte concentrations frequently necessary in salting-out, that might denature the proteins. Because membranes are now available with controlled pore sizes of relatively narrow spreads, it would seem simple to exploit differences in protein sizes by choosing materials which pass one species and retain others. The situation is not so simple however. Proteins frequently adsorb on surfaces, and the adsorption can depend on pH, salt concentration and other characteristics of the medium, as well as the nature of the membrane material. Even without difficulties from specific adsorption on the surface of the pores, proteins or other substances in the medium may form a fouling layer, or dynamic membrane, at the interface and make the nominal pore size of the membrane irrelevant. Interaction of proteins in the solution phase can cause further complications. When pore dimensions are of the same order of magnitude as particle sizes, co interactions between particles and pores can significantly affect rejection, by ion ("Donnan") exclusion mechanisms. These influences may be complex, because of the variation of the sign and magnitude of protein charge with pH, as well as similar variations of membrane charge from pH or fouling.

In spite of these difficulties, separations with membranes have been realized. Cordle et al., in U.S. Pat. No. 4,897,465, claim to reduce the ratio of beta-lactoglobulin and alpha-lactalbumin to immuno-gamma globulin (gG) and bovine serum albumin (BSA) in cheese whey by passing the first two and retaining the others, in a single ultrafiltration and subsequent diafiltration (adding pH-adjusted water or physiological saline solution to retentate and removing it and other permeating impurities by further ultrafiltration). Their separation was carried out at pH 5. The membrane they used was a porous, stainless steel tube with a bed of metal oxide particles. They adjusted the pH to 7, and in a second ultrafiltration, passed gG and BSA with the permeate, thus purifying them from bacteria, fat, casein and other such large retained species. Although they did not demonstrate enrichment of BSA and gG relative to one another, they stated that they believed this would be feasible at pH 5.5. They also claimed the reverse procedure, the first ultrafiltration at pH 7 with the desired proteins in the permeate, freed of large unwanted species, and the second ultrafiltration at pH 5, to concentrate gG and BSA and to remove unwanted small species in the permeate.

Central to their process was the concept that, with the filter they used, porous stainless steel with a layer of metal oxide particulates, proteins would be rejected at pH values below their isoelectric points and would permeate at pH values above. The isoelectric point (IEP) of gG is about 6.5 and of BSA about 4.8. The pH which they specify for expected (not demonstrated) separation is 5.5.

Ohno et al., in U.S. Pat. No. 4,347,138, were able to separate blood serum gamma globulin and albumin by ultrafiltration through a polysulfone membrane, stated to have a MW cutoff of 100,000. Large species had been removed prior to the ultrafiltration by centrifugation, and the volume was diluted to 1.5% total protein, salt added to 0.04M, and the pH adjusted to 4.1. Globulin was retained, but considerable albumin was passed when 80% of the volume had permeated. After several dilutions with buffer and subsequent ultrafiltration, most of the albumin was in permeate and most globulin in retentate.

Comparison of the recommended pH values in these two patents indicates that other factors must influence the results: Cordle et al. see no separation at pH 5, but believe that a more basic solution, pH 5.5, would be optimal, whereas Ohno et al. demonstrate separation at pH 4.1, on the acidic rather than the basic side of that used by Cordle, and specify a preferred range of 3.9–4.3. Differences in the membranes used and in bovine and human proteins are two of the many possible sources for differences in optimal separation conditions.

Roger et al. (in U.S. Pat. No. 4,485,040 and U.S. Pat. No. 4,711,953) fractionate alpha-lactalbumin in cheese whey by permeating it through a 50K MW cutoff membrane with pH adjusted to 6.6 to increase its passage, large species being retained; they then concentrated it and removed by low-molecular weight impurities by diafiltration through 2K MW cutoff membranes. Kolthe et al. (in U.S. Pat. No. 4,644,056) purify gG from milk or colostrum by diafiltering it through membranes of large pore size in a pH range of 4–5.5, and the permeate subjected to diafiltration with membranes of small pore size, low molecular weight species being removed. The pH range here at which gG permeates is the region used by Cordle et al. and Ohno et al. to retain it.

Although the specific differences in conditions responsible for the apparent contradictions in the teachings optimal for separations are not clear in all cases, the cited observations illustrate that protein passage and retention are complex phenomena, dependent on many factors.

SUMMARY OF THE INVENTION

The invention is directed to a method for the separation of gamma globulin from albumin contained in an aqueous solution of both by ultrafiltration using an altered substrate microfilter having a water permeability of 0.2–25 gallons per square foot per day per pound per square inch comprising a porous solid filter substrate one surface of which is impregnated with particulate solids affixed within the pores of the substrate having an average particle size of 0.10–0.50 micrometer at the feed interface, the aqueous solution being characterized in that the total concentration of protein in the aqueous solution is 0.1-2.0% by weight, the pH of the aqueous solution is 8-10 and the solution contains no more than 0.01 mole per liter of inorganic electrolyte, the albumin being enriched in the retentate and the gamma globulin being enriched in the permeate from the microfilter.

DETAILED DESCRIPTION OF THE INVENTION

The method of the invention is preferably carried out using an altered substrate microfilter. As used herein, the term "altered substrate microfilter" refers to a dimensionally stable porous solid filter substrate, one surface of which has been impregnated with particulate solids which are affixed within the pores of the substrate. The method by which the solids are affixed within the pores of the substrate is not critical. For example, particle solids may be affixed by sintering of the particles, by sintering of the substrate material and-/or by sintering of both the particles and the substrate material. A typical altered substrate is illustrated by the invention described and claimed in U.S. Pat. No. 4,888,114 to Gaddis et al. The materials of construction for altered substrate microfilter elements vary widely and include a wide variety of altered substrates including both metals such as stainless steel and ceramic materials. Porous structure of carbon or polymeric materials can also be used. Either low surface energy materials such as TEFLON ® fluoropolymers or high surface energy materials can be used. The precise composition of the substrate material is not critical so long as it possesses the proper degree of porosity, inertness with respect to the materials being processed and mechanical strength to withstand the mechanical stresses which are incident to normal filter operation and maintenance.

As is pointed out in the above-referred Gaddis et al. '114 patent, it is essential that the pores of the substrate be 0.5-10 micrometers in size in order to accommodate the particles within the pores prior to their being sintered. It is also preferred that the particle size of the substrate material be from 1 to 10 micrometers. If the particles are substantially more than 10 micrometers, the porous substrate tends to lose mechanical strength and is brittle. On the other hand, it is difficult to obtain adequate impregnation of the solids and the pressure drop through the substrate is likely to be excessive.

While it is preferred to use titanium oxide as the impregnating particulate solids, it will be recognized that other metal oxides and materials other than metal oxides can be used, e.g. polymer particles, $SiO_2$, metal, etc. It is also essential that the size of the particles to be sintered is sufficiently small that they can readily be deposited within the substrate pores by treatment with slurries of the solids before they are sintered to the substrate particles.

For more efficient operation of the filter, the impregnating solids should be impregnated and sintered within the porous substrate to a depth of 30-100 micrometers and should be as evenly distributed as possible. If the depth of the sintered metal oxide is too low, it tends to be weak mechanically and if the depth is too high, the length-to-diameter ratio of the paths through the substrate is too high and the pressure drop during operation of the filter tends to become excessively high as well.

In order to realize the maximum separation efficiency by use of the method of the invention, it is preferred to operate within the following ranges for the operating variables.

In particular, it is preferred that the water permeability of the filter be within the range of 0.2-25 gallons per square foot per day per pound per square foot and preferably 0.5-20. Above this range, the filter tends to pass both proteins and there is very little selectivity between the retentate and permeate.

Furthermore, while the aqueous mixture of proteins can contain a small amount of inorganic electrolytes, it is nevertheless preferred that they not exceed 0.1 M/L and still more preferably a maximum of 0.01 M/L. Because the aqueous mixture is likely to contain a small amount of natural electrolytes, it is still further preferred that none be added.

Unexpectedly, it was found that the total concentration of the proteins in the aqueous mixture has a significant effect on selectivity of the method. For this reason, it is preferred that the concentration of proteins be no more than 2.0 g/L and preferably no more than 1.0 g/L. Though not essential from the standpoint of operability, it is nevertheless preferred that the total concentration of proteins in the aqueous mixture be at least 0.1 g/L and still more preferably at least 0.5 g/L.

In view of the teaching of the prior art, it is particularly noteworthy that in the practice of the invention it has been found that if the pH of the aqueous solution of proteins is at least 8, the enrichment of the two proteins in the two fractions is enhanced. It is preferred that the pH not exceed 10.

The invention will be still further understood and is illustrated by the following examples.

EXAMPLES

EXAMPLES 1-10

In the following examples a series of tests was carried out to observe the effects of filter water permeability, protein concentration, salt addition and pH upon the efficacy of the altered substrate microfilter to separate bovine gamma-globulin (gG) and bovine serum albumin (BSA) from aqueous solutions thereof.

A series of ten experiments was performed using an apparatus comprising a feed reservoir having an outlet feed line connected to a feed pump having a feed line to an altered substrate filter impregnated with titanium dioxide particles. The outlet line from the pump contained a pressure gauge and the retentate line from the filter contained a control valve to regulate pressure of the feed in contact with the membrane. Both the permeate and retentate from the filter were returned to the feed reservoir after sampling. The albumin and gamma-globulin contents of the permeate and retentate were measured by gel permeation chromatography (GPC).

For the GPC analyses, a TSK-3000-SW column was used with a phosphate buffer composed of 0.1M sodium phosphate and 0.1M $NaNO_3$ adjusted to pH 6, at 0.5 mL/min. The retention times were 16.9 minutes for gamma-globulin (G) and 18.8 minutes for the bovine serum albumin (A). Circulation velocities for the system were 1.5-1.9 m/sec and pressures were 27-28 p.s.i.

The results of these tests are shown in Table 1 below.

The data from Example 1 show that when the filtration medium is "too loose", i.e. the water permeability (WP) of the microfilter is too high, the filter passes both proteins and there is little or no selectivity between the permeate and retentate. In addition, Examples 7 and 9 show that the addition of electrolyte salts, such as KCl, adversely affects the selectivity of the method at both high and low pH levels.

the isoelectric points of both proteins, BSA is enriched in the retained solution and gG in the permeate.

TABLE I

SEPARATION OF BOVINE SERUM ALBUMIN AND BOVINE GAMMA GLOBULIN BY ALTERED SUBSTRATE MICROFILTRATION

| Example No. | WP (gfd/psi) | pH | KCl (mM) | A in feed (g/l) | A in permeate (g/l) | G in feed (g/l) | G in permeate (g/l) | Passage* A | Passage* G |
|---|---|---|---|---|---|---|---|---|---|
| 1 | 64 | 6.1 | — | 0.53 | 0.53 | 0.33 | 0.31 | 1 | 0.94 |
| 2 | 17 | 4.8 | — | 2.89 | 0.25 | 1.60 | 0.08 | 0.09 | 0.05 |
| 3 | 15 | 8.3 | — | 2.88 | 0.21 | 1.64 | 0.38 | 0.07 | 0.23 |
| 4 | 17 | 4.9 | — | 0.23 | 0.16 | 0.21 | 0.023 | 0.70 | 0.11 |
| 5 | 13 | 8.4 | — | 0.51 | 0.002 | 0.27 | 0.09 | 0 | 0.33 |
| 6 | 4.0 | 5.2 | — | 0.31 | 0.24 | 0.16 | 0.032 | 0.77 | 0.20 |
| 7 | 3.3 | 5.1 | 18 | 0.46 | 0.14 | 0.38 | 0.11 | 0.30 | 0.29 |
| 8 | 6.0 | 8.2 | — | 0.44 | 0.001 | 0.65 | 0.15 | 0 | 0.23 |
| 9 | 4.1 | 8.2 | 18 | 0.46 | 0.13 | 0.36 | 0.11 | 0.28 | 0.31 |
| 10 | 3.2 | 8.4 | — | 0.43 | 0.043 | 0.31 | 0.11 | 0.10 | 0.35 |

*Passage of a protein is the ratio of the amount of that protein in the permeate to the amount of that protein in the feed.

The effect of protein concentration can be seen by comparing Examples 2 and 4, which were obtained at pH 4.8 and Examples 3 and 5, which were obtained at pH about 8.3. At both concentrations, significant separations were obtained. In particular, the BSA was enriched in the permeate at pH 4.8 and gG at pH 8.3. However, the selectivities were much higher at lower total protein concentrations. Furthermore, the passages were greater and less total fluid would therefore have to be passed through the filter medium to obtain a given degree of selectivity.

Example 5 was of special interest in that the permeate was exceptionally free of BSA with a high passage of gG.

Further tightening of the membrane from a WP of 10-15 to 3-4 did not appear to enhance the separation efficiency. In fact, some selectivity appeared to have been lost.

In summary, these data show that an enrichment of BSA relative to gG in the retentate can be attained. In particular, at a pH above 8, which is much higher than

I claim:

1. A method for the separation of gamma globulin from albumin contained in an aqueous solution of both by ultrafiltration using an altered substrate microfilter having a water permeability of 0.2-25 gallons per square foot per day per pound per square inch comprising a porous solid filter substrate one surface of which is impregnated with particulate solids affixed within the pores of the substrate having an average particle size of 0.1-0.5 micrometer at the feed interface, the aqueous solution being characterized in that the total concentration of protein in the aqueous solution is 0.1-2% by weight, the pH of the aqueous solution is 8-10 and the solution contains no more than 0.01 mole per liter of inorganic electrolyte, the albumin being enriched in the retentate and the gamma globulin being enriched in the permeate.

2. The method of claim 1 in which the particulate solids are titanium oxide particles.

3. The method of claim 1 in which the substrate is sintered stainless steel.

* * * * *